United States Patent [19]
Chu et al.

[11] Patent Number: 5,284,565
[45] Date of Patent: Feb. 8, 1994

[54] SAMPLE WELL INSERT WITH WEDGE-SHAPED PROFILE FOR ULTRA-THIN SLAB GELS IN ELECTROPHORESIS

[75] Inventors: Daniel Y. Chu, San Francisco; Elaine R. Mardis, Hercules, both of Calif.

[73] Assignee: Bio-Rad Laboratories, Inc., Hercules, Calif.

[21] Appl. No.: 995,495

[22] Filed: Dec. 23, 1992

[51] Int. Cl.$^5$ .................... G01N 27/26; G01N 27/447
[52] U.S. Cl. .............................. 204/299 R; 204/182.8
[58] Field of Search ......................... 204/182.8, 299 R

[56] References Cited

U.S. PATENT DOCUMENTS

| | | | |
|---|---|---|---|
| 4,883,577 | 11/1989 | Sugimoto et al. | 204/299 R |
| 5,073,246 | 12/1991 | Chu et al. | 204/299 R |
| 5,164,065 | 11/1992 | Bettencourt et al. | 204/299 R |

OTHER PUBLICATIONS

Douglas E. Kolner "Ultrathin DNA Sequencing Gels Using Microtrough Vertical Electrophoresis Plates" BioTechniques vol. 13, No. 3 (Sep. 1992) 338–339.

*Primary Examiner*—John Niebling
*Assistant Examiner*—John S. Starsiak, Jr.
*Attorney, Agent, or Firm*—Townsend and Townsend Khourie and Crew

[57] ABSTRACT

A comb to be used for holding samples and defining sample lanes in an ultra-thin slab gel in vertical slab gel electrophoresis is constructed with to form tapered or wedged-shaped sample wells, with the narrowest edge of the wedge opening into the upper edge of the gel. In one embodiment, the comb has a wedge-shaped profile along the contact edge to provide an expanded well at each sample location. Notches alternating with grooves are cut into the wedge shape to form teeth which taper along orthogonal axes, the wells being defined by the space between each adjacent pair of teeth. The gel enclosure which holds the slab gel is formed by plates which are shaped along one edge to provide a complementary wedge-shaped opening leading into the gel space. The comb fits snugly into the opening with the teeth of the comb touching or extending a short distance into the upper exposed surface of the gel. In another embodiment, the comb has a rectangular profile, with grooves cut to a varying depth to form the wedge shape.

8 Claims, 4 Drawing Sheets

SAMPLE WELL INSERT WITH WEDGE-SHAPED PROFILE FOR ULTRA-THIN SLAB GELS IN ELECTROPHORESIS

This invention lies in the field of vertical slab gel electrophoresis. In particular, this invention addresses problems associated with extremely thin slab gels, and the use of "combs" to provide a multitude of wells to receive the samples and to define the lanes which each sample will follow during its migration through the gel.

BACKGROUND OF THE INVENTION

Included among the many considerations in designing apparatus for vertical slab gel electrophoresis is the need to load samples in a reliable and reproducible manner, and in such a manner that a maximum number of samples can be separated simultaneously in a single gel, each with sharp band resolution.

Slab gels are usually formed by joining two glass plates together with spacers at both vertical edges to establish a gap of preselected thickness between the plates. The plates are clamped together along the vertical edges and a seal is placed along the open bottom edge. The gap is then filled with gel solution, and the gel is allowed to set. In some slab gels, a well-forming insert, referred to in the industry as a "comb" or a "template," is placed along the open upper edge of the gel solution before the gel sets, the teeth of the comb extending into the space between the plates. After the gel sets, the comb is removed to leave a row of wells formed in the gel along its top edge for sample loading.

In other slab gels, particularly those of less than 0.016 inch (0.40 mm) in thickness, a different type of comb is used, one which is placed between the gel plates after the gel has set, and is left in place during the electrophoresis. This comb is commonly referred to as a "sharkstooth comb" since its teeth are pointed. Once the gel has been set, the comb is inserted between the plates such that the tips of the comb's teeth contact the upper edge of the gel. Between the teeth of the comb are inverted V-shaped spaces, each of which is used as a well to receive a sample which is to be subjected to an electrophoretic separation.

In structures where sharkstooth combs are used, the plates which hold the gel often differ in height, with one plate extending a short distance above the other. The upper edge of the gel is located a short distance below the upper edge of the shorter plate. The sharkstooth comb is inserted between the plates in such a manner that the inverted V-shaped spaces between the teeth extend above the shorter plate but not the taller plate, which closes them on one side. Liquid sample aliquots are then introduced into the spaces at their open sides, flowing into the area between the plates above the gel, where they form individual pools separated by the teeth. Since the teeth are narrow at their pointed ends, the samples although separated are very close together, forming essentially contiguous lanes.

Extremely thin (ultra-thin) gels, i.e., gels of 0.005 inch (0.13 mm) do not permit the use of sharkstooth combs of the type described in the last paragraph. Combs of such thinness would be extremely delicate to handle and highly prone to damage, and the wells between the teeth would be so narrow that placing samples inside would be difficult if not essentially impossible.

These and other problems of a similar nature are addressed by the present invention.

SUMMARY OF THE INVENTION

The present invention provides a combination slab gel enclosure and sample comb, the sample comb containing troughs which, when the comb is inserted in the gel enclosure, form sample wells with a profile which tapers toward the gel. The wells are thus wide at the top to facilitate the introduction of a sample and to permit the retention of a sample of substantial size, and narrow at the bottom to direct the sample into the ultra-thin gel held between the plates.

In one embodiment, the enclosure walls expand outward along the edge where samples are introduced to form a wedge-shaped profile, and the sample comb has a complementary wedge-shaped profile along its toothed edge, to fit into the wedge formed by the gel enclosure walls. The teeth of the comb thus have a wedge-shaped profile (i.e., their cross section perpendicular to the plane of the comb). Between each adjacent pair of teeth is a groove or trough running perpendicular to the comb edge (parallel to the teeth), thereby forming a wedge-shaped sample well whose top has a front-to-back depth which is considerably greater than the width of the gel space where the slab gel is contained. By providing a wedge-shaped profile for both the gel enclosure and sample comb, all of the known benefits of a sharkstooth comb are achieved without the added problems associated with attempts to use a sharkstooth comb having the same thickness as an ultra-thin gel.

Included in preferred forms of the first embodiment is a wedge-shaped stopper bar which has a profile similar to that of the sample comb but is neither notched to form the teeth of the sample comb, nor grooved to form the sample troughs. The stopper bar fits inside the wedge formed by the walls of the enclosure in the same manner as the sample comb, but is used as a stopper during casting of the gel to provide the gel with a straight upper edge. Once the gel is cast, the stopper bar is removed and replaced with the sample comb, and samples are placed in the individual wells for electrophoresis.

In a second embodiment, the sample holder does not have a wedge-shaped profile, but instead has grooves which decrease in depth from one end to the other. The enclosure walls in this embodiment are of unequal height, and the sample holder rests on the top edge of the lower wall, with the tapered end of each groove lying directly above the gel space. A similarly shaped stopper bar, without the grooves, is included in preferred forms of this embodiment.

Other features, advantages and preferred embodiments of the invention will be apparent from the description which follows.

DETAILED DESCRIPTION OF THE INVENTION AND PREFERRED EMBODIMENTS

Figure 1:
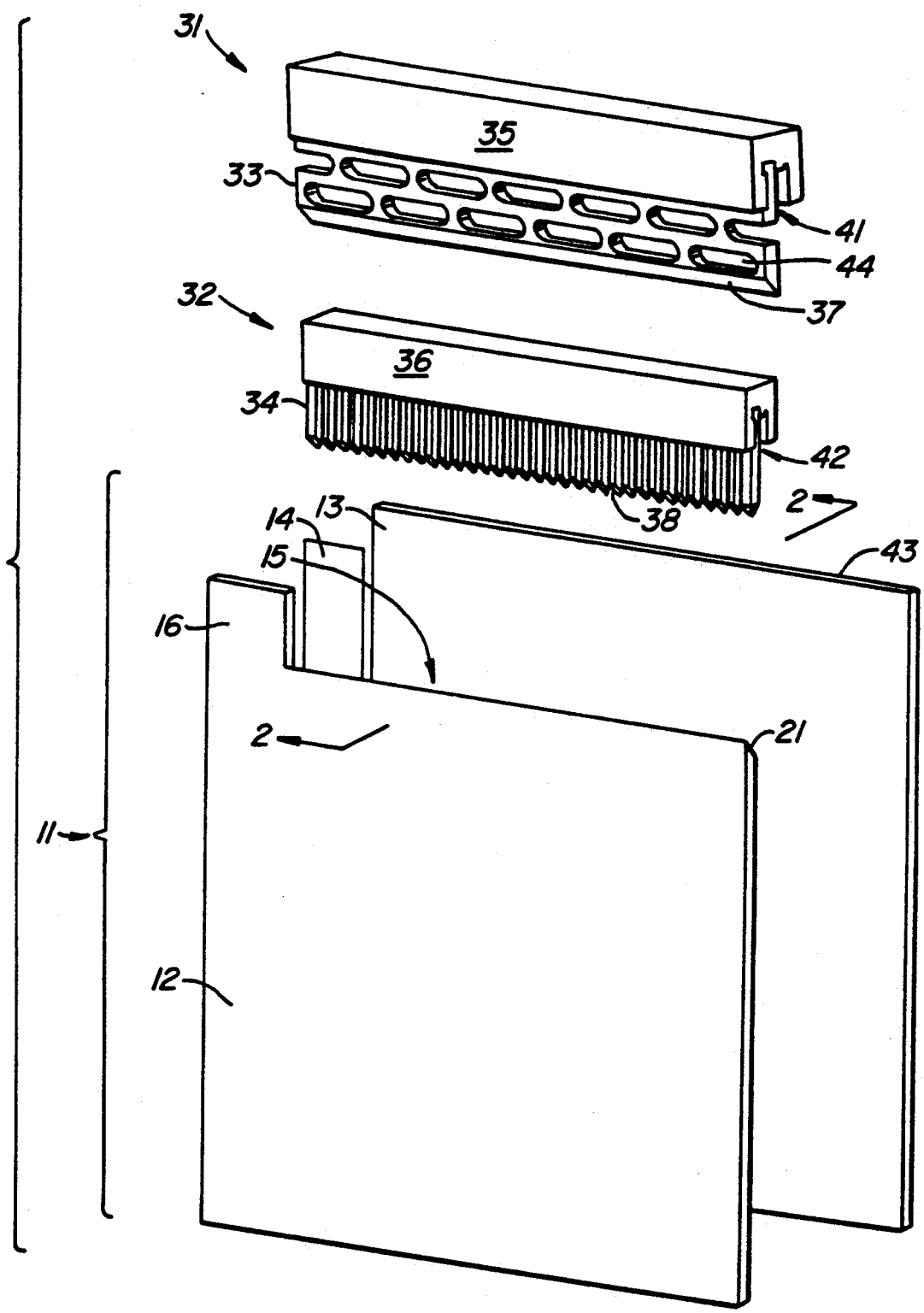
FIG. 1 is an exploded view of one end of one embodiment of the invention, showing the two transparent plates, one of the two spacer strips, and both the stopper bar and the sample holder comb.

The exploded half view of FIG. 1 shows the left half of a gel enclosure 11, consisting primarily of two transparent plates 12, 13 and a spacer strip 14. Of the two plates, one 12 has an indented central section 15 along one edge, so that the two plates are of different heights along this section when positioned vertically with this edge on top. This facilitates the formation of an upper buffer chamber (not shown) containing an electrode buffer solution which will be in contact with the upper edge of the gel between the plates. The configuration of such a chamber will be evident from FIG. 3 and is discussed in greater detail below. A shoulder 16 protruding upward from the left vertical edge renders the two plates of equal height along this edge. Note that this view is truncated on the right side, both plates continuing to the right beyond the Figure with a shoulder and spacer strip at the right edge (not shown) identical to those shown at the left edge.

As in conventional vertical slab gel enclosures, the spacer strip 14 and the corresponding strip at the right edge establish the width of the gap between the two plates and hence the thickness of the gel. In use, the two plates and the two spacer strips are held together by clamps (not shown in these drawings) along the two vertical edges, compressing the plates against the spacer strips. Various clamp configurations are known in the art and in general use, and any such clamp may be used in the structure shown in this drawing.

Figure 2:
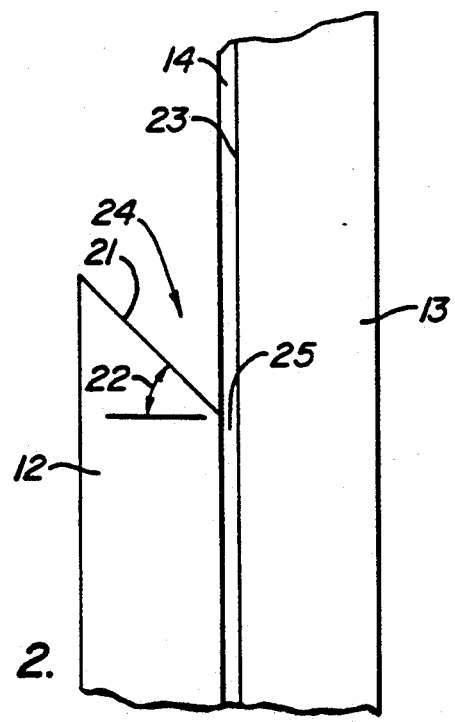
FIG. 2 is a side cross section view of the transparent plates and spacer strip of FIG. 1, taken along the line 2—2 of FIG. 1.

Both plates 12, 13 are flat-surfaced, except that the indented-edge plate 12 has an angled or bevelled edge 21 along the indented section 15. As seen in FIG. 2, this edge is at an acute angle 22 with the horizontal (i.e., with the axis normal to the plate surface). In FIG. 2, the two plates 12, 13 and the spacer strip 14 are shown in contact with each other, the bevelled edge 21 of the forward plate and the inner flat surface 23 of the rear plate 13 together forming a wedge-shaped opening 24 leading to the gel space 25 bounded by the two plates and the two spacer strips.

Returning to FIG. 1, two inserts are shown poised above the upper edge of the gel enclosure 11. One is the stopper bar 31 used during casting of the gel, and the other is the sample holder comb 32 used during electrophoresis. Both are identical in peripheral shape, the comb being distinguished by the grooves and notches referred to above, which are discussed in more detail below. The profile of each insert, i.e., the outline of the cross section taken along the plane parallel to the end edges 33, 34 of the inserts and perpendicular to the faces 35, 36, includes a bevelled or wedge-shaped lower edge 37, 38. These edges are at the same angle as the wedge-shaped opening 23 (FIG. 2) along the top edge of the gel enclosure, and as a result, each of the inserts fits snugly into the top of the gel enclosure. The insert profiles each further include an inverted trough 41, 42 to receive the upper edge 43 of the unindented plate 13. A pair of manually-operated screws (not shown in the drawing) in the rear surfaces of each insert (i.e., the surfaces opposite the broad surfaces shown in the drawing) serve to secure the insert into position and to stabilize it during use.

Figure 3:
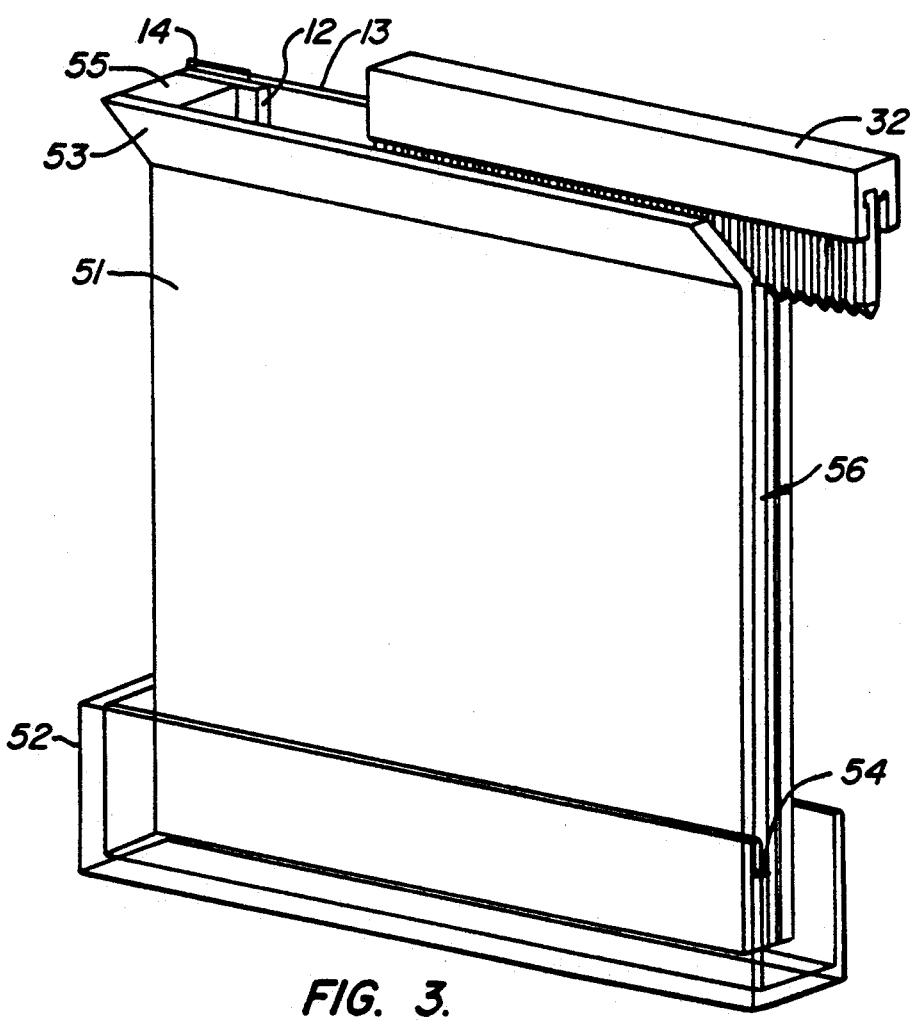
FIG. 3 is an assembled view of the parts shown in FIG. 1, minus the stopper bar but including additional parts used during an electrophoresis run.

The view in FIG. 3 shows the transparent plates 12, 13, spacer 14 and comb 32 assembled together with two additional parts—a shaped plate 51 to form the upper buffer chamber, and a reservoir 52 to form the lower buffer chamber.

The shaped plate has an outwardly angled upper edge 53, an inwardly protruding shoulder 54 along the lower edge, and an inwardly protruding shoulder 55 along the left side edge. A similar inwardly protruding shoulder runs along the right side edge, but since this view is truncated on the right side, this shoulder is not visible in the drawing. These shoulders 54, 55 define an open space 56 between the shaped plate 51 and the outer surface of the indented plate 12. The surfaces along these shoulders and down along the side edges of the shaped plate 51 which contact the outer surface of the indented plate 12 form a liquid-tight seal by means of an adhesive sealant or gasket (not shown). During electrophoresis, this open space 56 is filled with electrode buffer solution, and serves as the upper buffer chamber. The solution filling this space contacts the comb 32 and the upper edge of the gel.

The reservoir 52 is a trough-shaped receptacle, the view in the drawing being truncated on the right side, as in the other elements shown. During electrophoresis, the reservoir 52 is filled with a second electrode buffer solution and serves as the lower buffer chamber. The lower edges of the transparent plates 12, 13 forming the gel enclosure, and hence the lower edge of the gel itself, which is exposed, are immersed in the solution in this reservoir.

The method of assembling the plates and spacer strips to form what is commonly referred to as a gel sandwich, clamping a casting device onto the bottom of the gel sandwich, the device containing a central pore for introduction of gel solution, introducing gel solution through the pore into the gel space 24 (FIG. 2), inserting the stopper bar in the top of the gel sandwich and casting the gel, replacing the stopper bar with the comb, and placing the enclosure in an electrophoresis cell which includes the lower reservoir 52 and all necessary electrodes, power source, electrical connections, and controller and programmer if used, are all known in general terms in the art, and these art-recognized methods may be applied in the use of this apparatus.

Figure 4A:
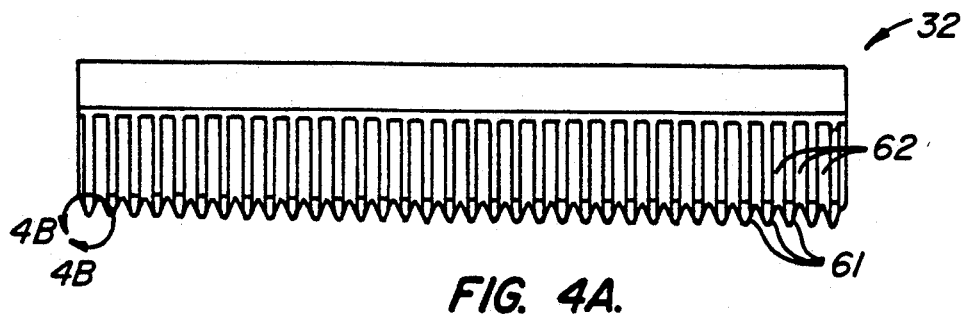
FIG. 4A is a front elevation view of a sample holder comb.

FIG. 4A shows the sample holder comb 32 in an enlarged view. The lower edge of the comb (according to the view shown in the drawing), which is the edge placed in contact with the gel slab, is notched to form the teeth 61 whose points mark the divisions between the individual sample lanes in the gel slab. Between each adjacent pair of teeth are grooves or troughs 62 which form wells in which the samples are placed.

Figure 4B:
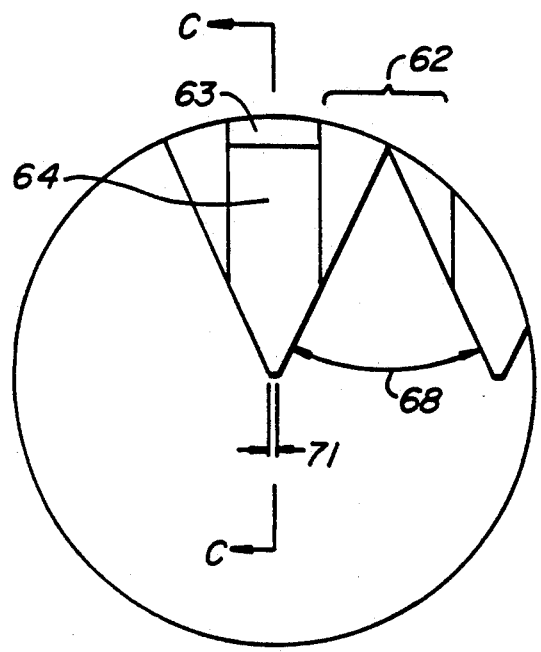
FIG. 4B is a detail view of the encircled portion of FIG. 4A.
Figure 4C:
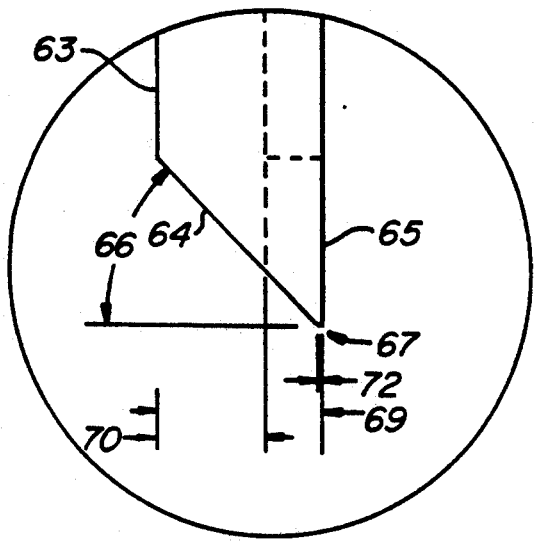
FIG. 4C is a cross section view taken along the line C—C of FIG. 4B.

In the detail view of FIG. 4B, two adjacent teeth are shown in the same view as that of FIG. 4A. This view is rotated 90° in FIG. 4C to show the tooth profile. As seen in FIG. 4B, the trough 62 is centered between two adjacent teeth. The forward surface of each tooth includes a surface portion 63 which is parallel to the plane of the comb as a whole, i.e., vertical when the comb is held vertically, and a surface portion 64 which is angled backward toward the rear surface 65 to form a tapering edge. The angle 66 of this angled surface portion 64 is identical to the angle 22 of the bevelled edge 21 of the forward gel enclosure plate 12 (see FIG. 2). Thus, when the tapering edge of the comb is inserted in the wedge-shaped opening 24 between the two plates (FIG. 2), the angled surface 64 and the rear surface 65 of the comb are in contact with the bevelled edge of the forward plate and the inner flat surface 23 of the rear plate, respectively. A sample well is thus formed which is as deep (i.e., as high, in the view shown in these drawings) as the height of the angled-surface sections of the teeth, and is defined by the space between the angled-surface sections of two adjacent teeth and between the bevelled edge 21 of the forward plate and the inner flat surface 23 of the rear plate.

The tip 67 of each tooth may be a sharp point or a blunt point, but will generally be sufficiently narrow that it protrudes into the gel space 25 (FIG. 2) between the two plates. Alternatively, if the tip is too broad to protrude into the gel space, it will still pierce the gel if the correspondingly tapered edge of the stopper bar 31 (FIG. 1) is even more blunt. In either case, the tips of the teeth will terminate lower (i.e., deeper into the gel) than the tapered edge of the stopper bar, to insure that the teeth pierce the gel when the comb is inserted. Except for the degree of bluntness of its tapered edge, the stopper bar 31 has the same cross sectional profile as the sample holder comb, except that it does not contain the tooth-forming notches or the grooves. The stopper bar in this embodiment does, however, contain a series of elongated holes 44 to impart lightness and flexibility to the stopper bar. This permits the stopper bar to be made of a relatively rigid material such as polyethylene.

Figure 5:
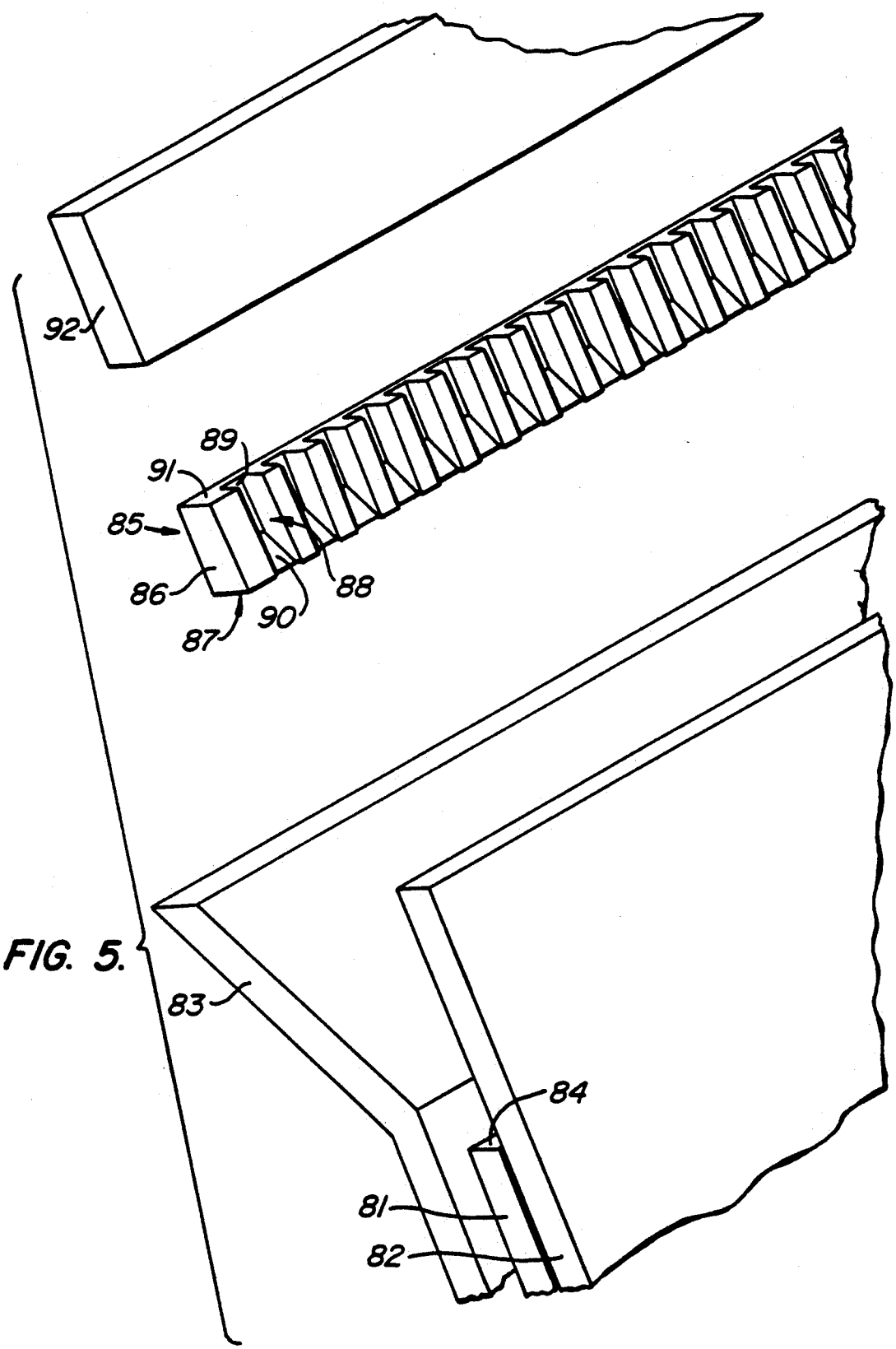
FIG. 5 is an exploded view of a second embodiment of the invention, showing the two transparent plates, a third plate forming the upper buffer chamber, and both the stopper bar and the sample holder comb.

An alternative embodiment of the present invention is shown in FIG. 5. Here, similar to the embodiment of the preceding Figures, the two transparent plates 81, 82 are of unequal height, with the upper buffer chamber formed by a shaped plate 83. In this embodiment, however, the shorter transparent plate 81 has a level or horizontal upper edge 84, rather than one which is outwardly angled.

The sample holder 85 has a rectangular profile, as indicated by the shape of its end edge 86, rather than a vevelled or wedge-shaped profile. The horizontal lower edge 87 of the sample holder rests on the horizontal upper edge 84 of the shorter plate and forms a water-tight seal. The grooves 88 in the sample holder open on the side facing the taller plate 82 of the gel enclosure rather than the shorter plate, and each groove has a tapering profile defined by a rear wall which is bifurcated into upper 89 and lower 90 segments. The depth of the groove at the upper edge 91 of the sample holder is thus greater than the depth at the lower edge 87, and the depth at the lower edge is generally very close to or slightly less than or more than the thickness of the gel as defined by the gap between the two plates 81, 82. A stopper bar 92 for this embodiment is likewise rectangular in cross section, with a thickness equal to that of the sample holder.

Not shown in the Figure but included in the structure are spacer strips, the reservoir for the lower buffer solution, and means for holding the parts together in a liquid-tight manner. These components may be the same as or similar to those shown in connection with the embodiment of the preceding Figures, or may be substituted by components whose construction will be readily apparent to those skilled in the art.

The dimensions and arrangement of the notches, grooves and other surface elements of the comb may vary widely within the scope of the invention. When plates of unequal height as shown in the Figure are used, the thickness of the comb is preferably substantially equal to or greater than the thickness of the short plate. The combs will generally have at least ten grooves, preferably at least thirty, thereby forming an equal number of sample wells. In a presently preferred embodiment, the comb and plates have the configuration of FIGS. 1-4C, the comb having a total width of 5.78 inches (14.68 cm), with 34 teeth 61, the points 67 of the teeth separated by a spacing of 0.170 inch (4.32 mm); the angle 22, 66 of the bevelled edge and the angled surfaces of the teeth is 45°, and the angle 68 between adjacent teeth (FIG. 4B) is 53°; the thickness of the comb 69 is 0.187 inch (4.75 mm); the depth 70 of each groove or trough is 0.127 inch (3.23 mm); the width 71 of the blunted end of each tooth is 0.006 inch (0.15 mm); and the depth 72 of the blunted end of each tooth is 0.003 inch (0.076 mm). The dimension on the blunted tapered edge of the stopper bar 31 corresponding to the depth 72 of the blunted end of each tooth is 0.018 inch (0.46 mm).

Combs of the type described herein can be used for slab gels of any thickness, but will find particular utility with slab gels of a thickness of 0.005 inch (0.127 mm) or less, notably gels of a thickness ranging from about 0.001 inch (0.0254 mm) to about 0.004 inch (0.102 mm). As indicated above, the thickness of the gel is defined by the spacer strips used.

The material from which the comb and the stopper bar are made is not critical and may vary widely, subject only to the ability to be formed into the desired shape, to form a relatively water-tight seal when placed in contact with the transparent plates to form the sample wells, an to be inert to all materials which will come in contact with the comb and stopper bar during use, and to permit the gel solution to polymerize without inhibiting the polymerization reaction. A presently preferred material is hard rubber for the comb and polyethylene for the stopper bar. The transparent plates and the remaining components of the apparatus are made of conventional materials, whose only consideration is that they are sufficiently rigid to maintain their shape during use, and are electrically non-conductive and chemically inert to all materials with which they will come in contact during use. Glass or polymers such as polycarbonate will generally suffice.

The foregoing is offered primarily for purposes of illustration. It will be readily apparent to those skilled in the art that the materials, shapes, arrangements, configurations, and other parameters of the comb, stopper bar, and transparent plates, as well as any other components of the electrophoresis apparatus in which these components are used, may be further modified or substituted in various ways without departing from the spirit and scope of the invention.

What is claimed is:

1. A combination slab gel enclosure and liquid sample holder for use in electrophoretic separations of samples in slab gels having a thickness of less than about 0.005 inch, said combination comprising:
    a slab gel enclosure comprised of a pair of plates joined at two opposing edges by spacing means to define a slab-shaped gel space, and open at a third edge, said plates shaped along said third edge to form an expanded opening communicating with said slab-shaped gel space, said expanded opening being wedge-shaped along a cross section perpendicular to said slab-shaped gel space; and a liquid sample holder comprised of a member with an elongated edge of wedge-shaped cross section complementary to said cross section of said expanded opening, said elongated edge being notched to form regularly spaced sharp points and grooved between said sharp points to form discrete wells for liquid sample retention when said elongated edge is inserted in said expanded opening.

2. A combination in accordance with claim 1 in which said pair of plates are defined as first and second plates, said first plate being planar at said expanded opening and said second plate having a beveled inner surface at said expanded opening, thereby forming a wedge-shaped cross section.

3. A combination in accordance with claim 2 in which said first and second plates are uneven along said third edge of said slab gel enclosure, said first plate extending beyond said second plate.

4. A combination of components for forming and retaining a slab gel having a thickness of less than about 0.005 inch and positioning liquid samples along an edge of said slab gel for electrophoretic separations, said combination comprising:

a slab gel enclosure comprised of a pair of plates joined at two opposing edges by spacing means to define a slab-shaped gel space, and open at a third edge, said plates shaped along said third edge to form an expanded opening communicating with said slab-shaped gel space, said expanded opening being wedge-shaped along a cross section perpendicular to said slab-shaped gel space;

a stopper bar comprised of a member with an elongated edge sized to fit within said expanded opening and to close off said slab-shaped gel space when inserted therein, said elongated edge being of wedge-shaped cross section complementary to said cross section of said expanded opening, to close off said slab-shaped gel space; and a liquid sample holder comprised of a member with an elongated edge of wedge-shaped cross section complementary to said cross section of said expanded opening, said elongated edge being notched to form regularly spaced sharp points and grooved between said sharp points to form discrete wells for liquid sample retention when said elongated edge is inserted in said expanded opening.

5. A combination slab gel enclosure and liquid sample holder for use in electrophoretic separations of samples in slab gels having a thickness of less than about 0.005 inch, said combination comprising:

a slab gel enclosure comprised of a pair of plates each having edges defined, when said slab gel enclosure is vertically oriented, as two side edges, a bottom edge and a top edge, corresponding side edges of said pair of plates being joined by spacing means to define a vertically oriented slab-shaped gel space, and the top edges of said plates being of uneven height with an opening in between permitting access to said gel space; and a liquid sample holder comprised of an elongated bar defined by an elongated top edge, an elongated bottom edge, side edges, and elongated front and rear surfaces, said elongated bar having a rectangular cross section and a series of grooves in said front surface and open at said top and bottom edges, each of said grooves having a depth which is greater at said top edge than at said bottom edge, the depth at said bottom edge being substantially equal to the thickness of said spacing means.

6. A combination in accordance with claim 5 in which said pair of plates are defined as a shorter and a taller plate, and in which the thickness of said liquid sample holder, defined as the distance between said front and rear surfaces, is substantially equal to or greater than the thickness of said shorter plate.

7. A combination in accordance with claim 5 in which each said groove is defined by a rear wall and two side walls, said rear wall being bifurcated into upper and lower sections, said upper section being parallel to said rear surface of said liquid sample holder, and said lower section forming an acute angle with said rear surface.

8. A combination in accordance with claim 5 in which said grooves are regularly spaced at intervals of less than 0.25 inch, and are at least ten in number.

* * * * *